(12) United States Patent
Gabbay

(10) Patent No.: US 6,638,285 B2
(45) Date of Patent: Oct. 28, 2003

(54) BIOLOGICAL TISSUE STRIP AND SYSTEM AND METHOD TO SEAL TISSUE

(76) Inventor: Shlomo Gabbay, #1 Randall Dr., Short Hills, NJ (US) 07078

(*) Notice: Subject to any disclaimer, the term of this patent is extended or adjusted under 35 U.S.C. 154(b) by 351 days.

(21) Appl. No.: 09/835,744

(22) Filed: Apr. 16, 2001

(65) Prior Publication Data
US 2002/0151911 A1 Oct. 17, 2002

(51) Int. Cl.⁷ .............................................. A61B 17/04
(52) U.S. Cl. ...................................... 606/151; 606/139
(58) Field of Search ................................ 606/139, 151; 227/19

(56) References Cited

U.S. PATENT DOCUMENTS

| | | | |
|---|---|---|---|
| 4,930,674 A | 6/1990 | Barak | 227/179 |
| 5,116,349 A | 5/1992 | Aranyi | 606/142 |
| 5,141,144 A | 8/1992 | Foslien et al. | 227/176 |
| 5,263,629 A | 11/1993 | Trumbull et al. | 227/181 |
| 5,368,599 A | 11/1994 | Hirsch et al. | 606/139 |
| 5,397,324 A | 3/1995 | Carroll et al. | 606/139 |
| 5,441,193 A | 8/1995 | Gravener | 227/176 |
| 5,503,638 A | 4/1996 | Cooper et al. | 623/11 |
| 5,542,594 A | 8/1996 | McKean et al. | 227/178.1 |
| 5,549,628 A | 8/1996 | Cooper et al. | 606/220 |
| 5,575,803 A | 11/1996 | Cooper et al. | 606/151 |
| 5,908,427 A * | 6/1999 | McKean et al. | 606/139 |
| 6,099,551 A | 8/2000 | Gabbay | 606/219 |

FOREIGN PATENT DOCUMENTS
WO  WO9838923  9/1998

OTHER PUBLICATIONS

Fischel, Richard J., et al. "Bovine Pericardium Versus Bovine Collagen to Buttress Staples for Lung Reduction Operations". *The Society of Thoracic Surgeons*. Published by Elsevier Science, Inc. 1998; 65: 217–9.

Cooper, Joel D. M.D. "Technique to Reduce Air Leaks After Resection of Emphysematous Lung". *The Annals of Thoracic Surgery*, by The Society of Thoracic Surgeons. Apr. 1994; vol. 57: No. 4.

Juettner, F.–M, M.D., et al. "Reinforced Staple Line in Severely Emphysematous Lungs". *Journal of Thoracic Cardiovascular Surgery*. 1989; 97: 362–3.

* cited by examiner

Primary Examiner—Gary Jackson
(74) Attorney, Agent, or Firm—Tarolli, Sundheim, Covell & Tummino L.L.P.

(57) ABSTRACT

A strip for use with a surgical stapler facilitates sealing tissue of a patient, such as the lungs, stomach, etc. The strip includes retaining elements near opposed ends of the strip for connecting to associated parts of a surgical stapler device. An aperture also extends through the strip at a location intermediate its opposed ends for receiving an alignment feature of the surgical stapler.

In another aspect, a second elongated strip having retaining elements near opposed ends thereof may be utilized in conjunction with the strip and a surgical stapler to seal the patient's tissue. In addition, the strips may be connected together by a bridge of material to facilitate selection and use of appropriate strips.

28 Claims, 4 Drawing Sheets

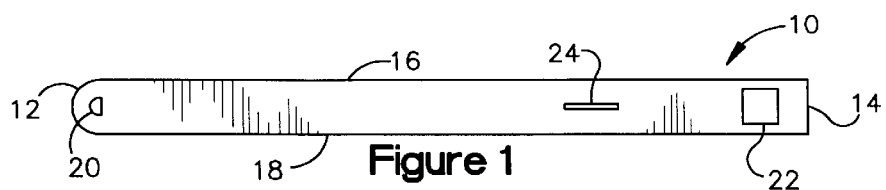
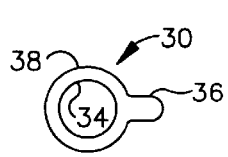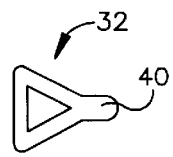
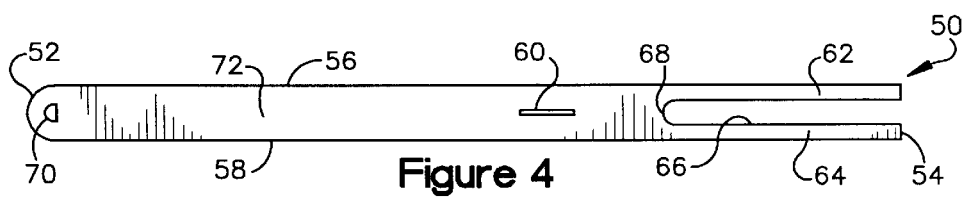
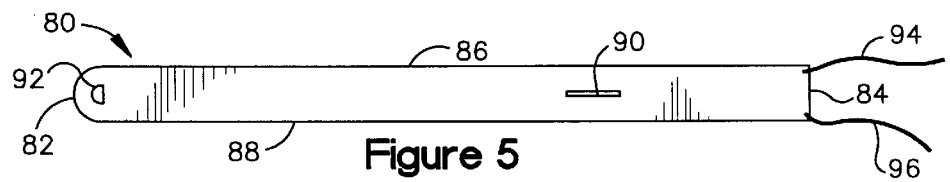
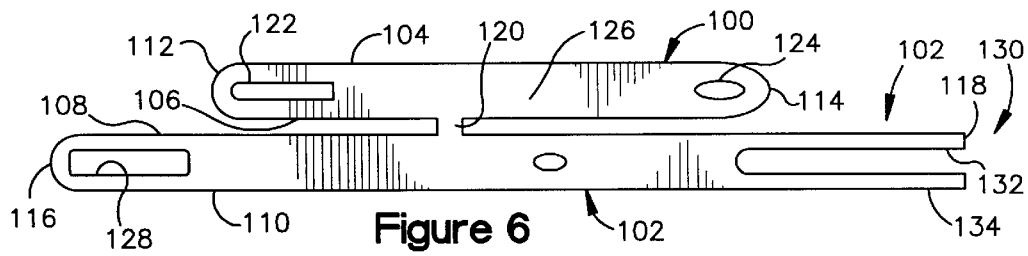
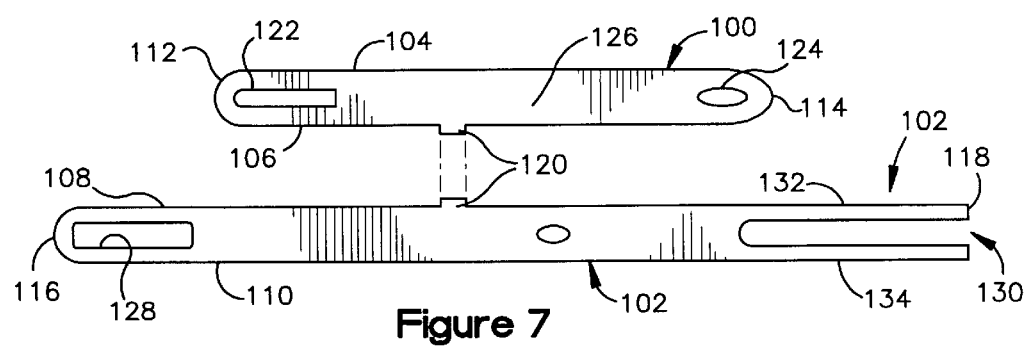

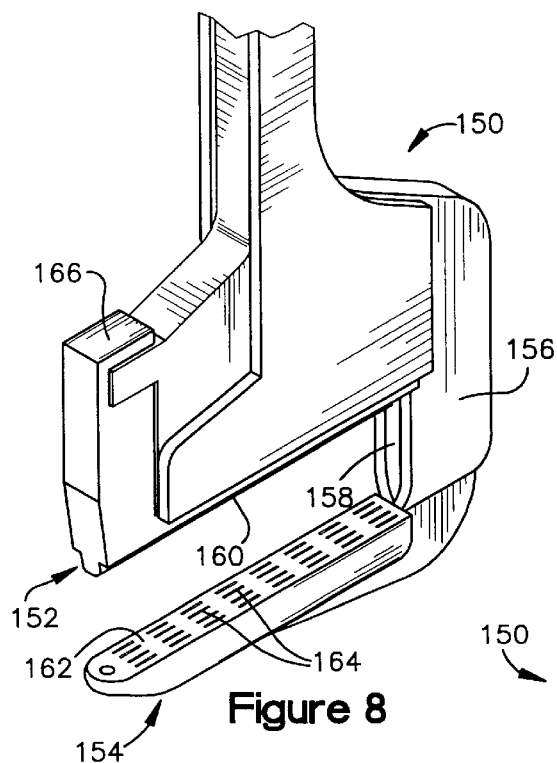
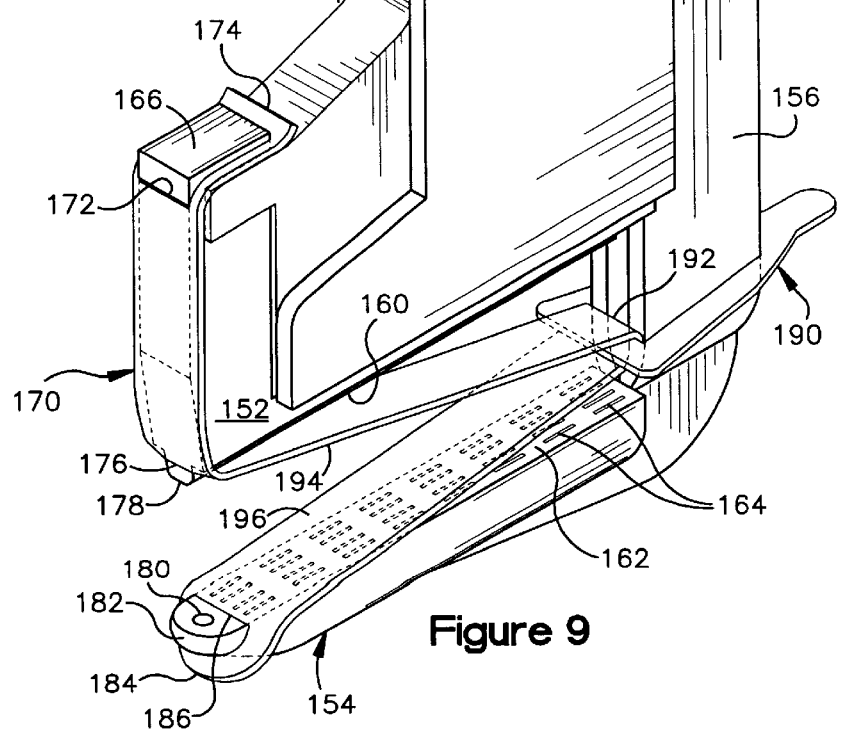

BIOLOGICAL TISSUE STRIP AND SYSTEM AND METHOD TO SEAL TISSUE

TECHNICAL FIELD

The present invention relates to a strip of biological tissue and to a system and method that may be employed to seal tissue.

BACKGROUND

It has been known to use stapling devices to seal visceral tissue upon resection thereof. However, stapling of the lungs can result in an air leak, which is detrimental to the health of the patient. This is especially true when the resection is used to accomplish "lung reduction". Since the lung reserves of such patients are very limited, even a small air leak can be detrimental and, in some circumstances, even fatal. Similar issues relating to leaks may occur during gastric reduction or bypass procedures. That is, if the stomach and/or intestinal tract are not sufficiently sealed during a gastric bypass procedure, some of the stomach fluids could leak into the abdominal cavity and, in turn, cause infection or other conditions.

In order to minimize the foregoing problem, pericardial or collagen tissue has been used in conjunction with a surgical stapler. Typically, the pericardial tissue is retained on the jaws by a cloth or plastic sleeve. However, this makes the procedure cumbersome and awkward. The foregoing is particularly true if the procedure is endoscopic. In other circumstances, an adhesive material may be employed to temporarily hold the tissue on the jaws of the stapler.

A surgical stapler includes three principal parts. One contains the staples, the other constitutes an anvil which receives the staples and initiates bending them in the proper direction, and the third, which is optional, is a knife which puts the final bend on the staples and cuts the tissue where desired.

A surgical stapler usually is designed to insert either two or four rows of staples, which are spaced apart from each other in a direction perpendicular to a longitudinal axis of the stapler jaws. In certain cases, a knife may be employed to cut between the rows of staples to longitudinally divide tissue on opposed sides of the staple lines.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

One aspect of the present invention provides a strip that may be utilized with a surgical stapler, such as to seal and divide selected tissue of a patient. The strip is formed of an elongated sheet of flexible, biocompatible material, such as treated biological material (e.g., pericardium, collagen, etc.). The elongated sheet has a leading end spaced apart from a trailing end by an elongated intermediate portion. Retaining elements are located adjacent the leading and trailing ends of the sheet for retaining the respective ends relative to parts of the surgical stapler. The sheet also includes an aperture that extends through the intermediate portion of the sheet at a location between the retaining elements, which aperture is operative to receive an alignment feature of the surgical stapler.

Another aspect of the present invention provides a system that may be used with a surgical stapler. The system includes first and second strips of biocompatible tissue material. The first strip includes leading and trailing ends spaced apart from each other by an elongated intermediate portion. First and second retailing elements are associated with the respective leading and trailing ends of the first strip to retain respective ends of the first strip relative to part of the surgical stapler. An aperture extends through the intermediate portion of the first strip at a position between the first and second retaining elements to receive an alignment feature of the surgical stapler. The second elongated strip also includes a leading end spaced apart from a trailing end by an elongated intermediate portion. First and second retaining element are located adjacent the respective leading and trailing ends of the second strip to retain respective ends of the second strip relative to part of the surgical stapler. A bridge of material may interconnect the first and second strips, which bridge may be cut to provide a pair of strips for use with the surgical stapler.

According to another aspect of the present invention, one or more strips may be attached to opposed jaws of a surgical stapler for sealing and or dividing selected tissue that may be positioned between the jaws. For example, when a single elongated strip is employed, ends of the strip are attached the distal ends of opposed jaws of the stapler. A retaining ring is utilized to urge an intermediate section of the strip away from the distal ends, such that different segments of the strip on opposed sides of the ring are oriented generally coextensively with faces of the respective jaws. By way of further example, when two strips are employed, each strip is mounted generally coextensively relative to a face of a different jaw. As a result, tissue interposed between the strips or strip segments may be stapled by actuating the stapler.

BRIEF DESCRIPTION OF THE DRAWINGS

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings, in which:

FIG. 1 is an example of a biological tissue strip configured for use with a surgical stapler in accordance with the present invention;

FIG. 2 is an example of a retaining ring for use with a biological tissue strip in accordance with the present invention;

FIG. 3 is an example of another retaining ring for use with a biological tissue strip in accordance with the present invention;

FIG. 4 is an example of another biological tissue strip configured for use with a surgical stapler in accordance with the present invention;

FIG. 5 is an example of another biological tissue strip configured for use with a surgical stapler in accordance with the present invention;

FIG. 6 is an example of a pair of biological tissue strips configured for use with a surgical stapler in accordance with the present invention;

FIG. 7 is an example of the tissue strips of FIG. 6 which have been cut prior implantation;

FIG. 8 is an example of a surgical stapler;

FIG. 9 depicts a biological tissue strip attached to the surgical stapler of FIG. 8 for use in accordance with the present invention;

DESCRIPTION OF THE INVENTION

Figure 10:
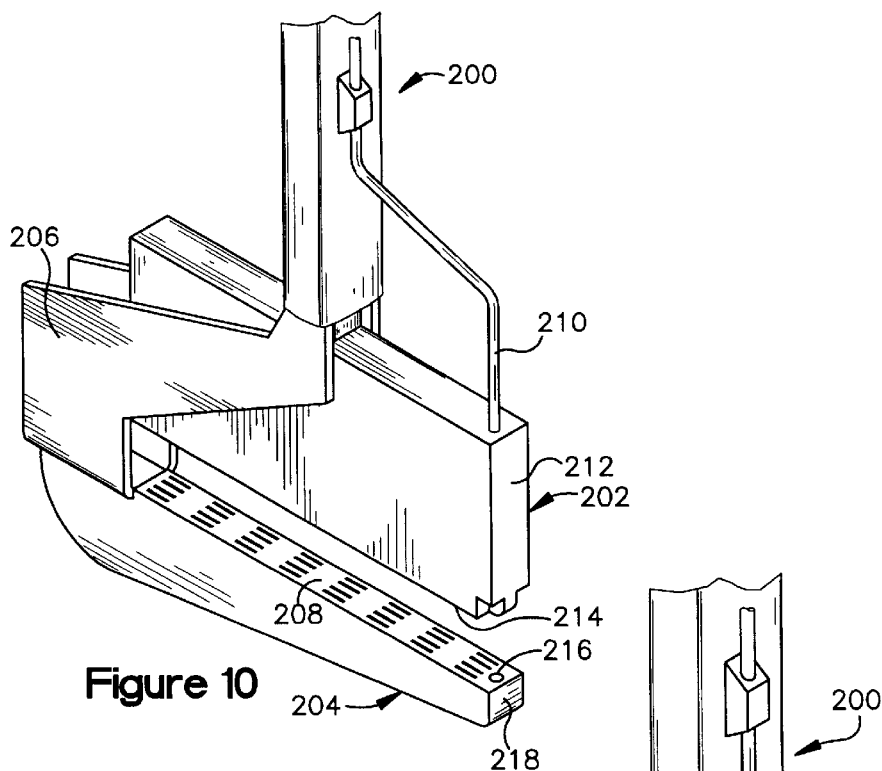
FIG. 10 is an example of another type of surgical stapler.

The present invention provides a strip for use with a surgical stapler to facilitate sealing tissue of a patient, such as the lungs, stomach, vascular tissue, etc. The strip includes retaining elements near its opposed ends for connecting to associated parts of a surgical stapler device. An aperture also extends through the strip at a location intermediate its opposed ends for receiving an alignment feature of the surgical stapler.

FIG. 1 illustrates an example of an elongated strip 10 of a biological tissue material in accordance with an aspect of the present invention. The strip 10 includes ends 12 and 14 spaced apart from each other by elongated side edges 16 and 18. A retaining element is located near each of the ends 12 and 14, which is operative to hold each respective end of the strip relative to an adjacent part of a surgical stapler.

In the example of FIG. 1, the retaining elements are depicted as apertures 20 and 22 extending through the sheet near the respective ends 12 and 14. Each of the apertures 20 and 22 is dimensioned and configured to mount to a corresponding structural component of a surgical stapler.

By way of illustration, the aperture 20 may be a semicircular or rectangular aperture dimensioned or otherwise configured to fit over part of a jaw of a surgical stapler. The other aperture 22, for example, may be dimensioned and configured to mount over a protruding structure associated with the opposite jaw of the surgical stapler.

The strip 10 also includes a slot 24 interposed between apertures 20 and 22. The aperture 24, for example, is an elongated slot extending longitudinally between the ends 12 and 14. The length and width of the slot 24 provides an opening to permit a rod or alignment pin of a surgical stapler to protrude through the slot when attached to the stapler. A portion of the strip 10 intermediate the slot 24 and aperture 20 provides for a length of material through which the staples may be urged to seal tissue in accordance with an aspect the present invention.

The strip 10 is formed of a flexible, biological tissue material, such as animal pericardium (e.g., bovine, porcine, equine, human, etc.), collagen or other suitable, biocompatible biological tissue material. The natural tissue material may be chemically treated in a suitable fixation solution, such as including glutaraldehyde, to improve the biocompatibility and texture of the material. In addition, the strip 10 may undergo a tissue detoxification process, such as is available through Shelhigh, Inc. of Milburn, N.J.

By way of further illustration, the tissue strip 10 may be formed from a length of NO-REACT® tissue, which is commercially available from Shelhigh, Inc., of Millburn, N.J. The NO-REACT® tissue helps improve the biocompatibility of the resulting prosthesis strip 10, thereby mitigating the likelihood of a patient rejecting the strip after being implanted. The NO-REACT® tissue also resists calcification.

It is to be understood and appreciated that other types of biocompatible materials (e.g., any biological tissue, collagen, as well as other natural tissue or synthetic materials) could be configured to provide a tissue strip in accordance with the present invention.

Additionally, the strip 10 may be stored in a wet or dry condition. For example, if the material is to be stored in a dry condition, the strip may be immersed in a solution of glycerin or other suitable material that may penetrate the tissue thereof. For example, a solution of about 5% to about 25% glycerin may be utilized. The strip may be immersed in the glycerin solution for about one to about five hours. After being treated in the glycerin solution, the strip 10 is dried, such that most aqueous moisture is removed. Advantageously, some of the glycerin remains embedded within the tissue so as to render the tissue pliable to facilitate its use in combination with a surgical stapler. Those skilled in the art will further understand and appreciate other suitable solutions that may be utilized to maintain the tissue material in a pliable condition after drying.

FIGS. 2 and 3 illustrate examples of different retaining rings 30 and 32, respectively, which may be utilized in combination with the strip 10 of FIG. 1 to help retain or hold part of the strip relative to a surgical stapler. The retaining rings 30 and 32 may be formed of a biological tissue material, which may be the same type of material as described above with respect to the strip of FIG. 1. Alternatively, retaining rings may be formed of different materials that have been appropriately sterilized.

In the example of FIG. 2, the retaining ring 30 is illustrated as an annular ring of material having an inner generally circular edge 34 that defines an aperture extending through the ring. A tab or finger 36 protrudes radially outwardly from an outer edge 38 of the ring 30. The tab 36 may be gripped by a surgeon or technician to facilitate urging the ring 30 over the strip 10 and part of a jaw of a surgical stapler, such as to urge part of the strip between the slot 24 and aperture 20 away from the slot and aperture (FIG. 1).

The retaining ring 32 of FIG. 3 is illustrated as having a generally triangular shape in which the juncture between two of the legs of the triangle is extended to define a tab 40. A generally triangular aperture extends through the ring 32 for receiving part of a surgical stapler. The tab 40 may be gripped by a surgeon or other technicians to facilitate urging the retaining tab over part of a jaw of a surgical stapler the tissue strip 10 (FIG. 1). Examples of the use of such a tab is shown and described below with respect to FIG. 9.

FIG. 4 illustrates an example of another strip 50 configured for use with a surgical stapler in accordance with an aspect of the present invention. The strip 50 includes end portions 52 and 54 spaced apart from each other by elongated side edges 56 and 58. A slot 60 extends longitudinally through the strip 50 at a location between the ends 52 and 54. The slot 60 is dimensioned and configured for receiving a rod or alignment pin of a surgical stapler. Retaining elements also are located near each of the ends 52 and 54 to hold each respective end of the strip relative to an adjacent part of a surgical stapler.

In accordance with an aspect of the present invention, the retaining element associated with the end 54 includes a pair of elongated ribbons 62 and 64 of flexible material. In a particular aspect, the ribbons 62 and 64 are integral with the body of the strip 50 and, thus, formed of the same tissue material. For example, the ribbons may be formed by cutting an elongated channel 66 that intersects the end 54 and extends from the end toward the slot 60 terminating at a location 68 between the end 54 and the slot 60. Because the ribbons 62 and 64 are formed of a flexible material, they may be tied around an adjacent part of the surgical stapler to releasably secure the portion 68 of the strip 50 adjacent the slot 60 at a desired position relative to the surgical stapler.

The strip 50 also includes another retaining element, illustrated as an aperture 70, which extends through the strip near the other end portion 52. While the aperture 70 is illustrated as having a generally semi-circular configuration, it will be understood and appreciated that other shapes also could be utilized in accordance with an aspect of the present invention.

The portion of the strip 50 extending longitudinally between the slot 60 and the aperture 70 defines an intermediate portion 72 of the strip that is employed to perform a desired sealing function. In a situation where the strip 50 is applied to cover a single jaw of a surgical stapler, the intermediate portion 72 covers at least a substantially portion of that jaw. In contrast, where the strip 50 is applied to both jaws of a stapler, one part of the intermediate portion 72 proximal the end 52 generally covers (e.g., substantially coextensive with) a face of one jaw and another part of the intermediate portion proximal the slot 60 generally covers a face of the other jaw. When the strip 50 is utilized to cover both jaws, a retaining ring, such as the rings 30 or 32 shown and described with respect to FIGS. 2 and 3, also may be utilized in conjunction with the strip 50 to position the strip at a desired orientation relative to the surgical stapler. As a result, the opposed parts of the intermediate portion 72 are generally coextensive with respective faces of the jaws.

FIG. 5 illustrates another example of another strip 80 configured for use with a surgical stapler in accordance with an aspect of the present invention. Similar to the strips of FIGS. 1 and 4, the strip 80 includes end portions 82 and 84 spaced apart from each other by generally parallel and elongated side edges 86 and 88. The strip 80 also includes a slot 90 extending longitudinally through the strip 80 at location between the ends 82 and 84 for receiving a rod or alignment pin of a surgical stapler. An aperture 92 is formed through the strip 80 near one end 82 of the strip to define a first retaining element, which is operative to releasably secure the end 82 to part of a surgical stapler.

A pair of elongated cords 94 and 96 extends from the strip 80 near the other end 84 to define a second retaining element. By way of illustration, the elongated cords 94 and 96 may be formed of a flexible material, such as a relatively thick suture material sewn through the strip near the end 84. Those skilled in the art will understand and appreciate other materials that may be utilized to provide adequate mechanisms to secure the end of the strip relative to a surgical stapler. The cords 94 and 96 thus may be tied around an adjacent part of a surgical stapler to help hold the strip 80 relative to the stapler. Advantageously, the cords 94 and 96 may be of any length sufficient to attach the end 84 relative to part of virtually any surgical stapler.

In accordance with an aspect of the present invention, cords may be applied to an end of a strip (e.g., the strip of FIGS. 1, 4 or 5) by a technician or surgeon just prior to implantation to facilitate attachment to the surgical stapler. While the strip 80 is illustrated as having an aperture 92 at one end and cords 94 and 96 at the other for securing the strip relative to the surgical stapler, it is understood and appreciated that similar cords (FIG. 5) or ribbons (FIG. 4) could be utilized at one or both ends of the strip to help secure the strip relative to a surgical stapler.

FIG. 6 illustrates an example of a pair of interconnected biocompatible tissue strips 100 and 102 that may be utilized in connection with a surgical stapler to promote sealing of tissue in accordance with an aspect of the present invention. In this example, each of the strips 100 and 102 is a sheet of a biocompatible material having elongated side edges 104, 106 and 108, 110 that extend between respective ends 112, 114 and 116, 118. A bridge 120 of material interconnects and extends between side edges 106 and 108 of the respective strips 100 and 102.

In accordance with a particular aspect, the strips 100 and 102 and the bridge 120 are all formed from an integral sheet of flexible material. The type of material from which the strips 100 and 102 and bridge 120 are formed may be substantially identical to that described with respect to FIG. 1. Because the strips 100 and 102 are secured together by the bridge 120, manufacture and storage of the strips are facilitated. In addition, a surgeon or technician may more easily obtain an appropriate pair of strips from storage, such as a container including a plurality of such interconnected strip pairs.

In the example of FIG. 6, the strip 100 includes retaining features 122 and 124 operatively associated with the strip near each of the ends 112 and 114 for releasably securing the respective ends relative to part of a surgical stapler. Specifically, the retaining feature 122 is depicted as an aperture extending through the strip 100. Similarly, the retaining feature 124 is illustrated as an aperture extending through the strip 100. An intermediate portion 126 of the strip 100 extending between the retaining features 122 and 124 provides a pledget of the tissue material that may engage a jaw of a surgical stapler during a stapling procedure and, in turn, promote sealing of tissue.

The strip 102 includes retaining features 128 and 130 near its respective ends 116 and 118 adapted to releasably secure the strip to another part of the surgical stapler. The retaining feature 128 is illustrated as a generally rectangular aperture extending through opposed surfaces of the strip 102 and the other retaining feature 130 includes a pair of elongated tissue ribbons 132 and 134, similar to the example shown and described in FIG. 4.

It is to be appreciated that other shapes and configurations of retaining features could be implemented at the ends of the strips 100 and 102 in accordance with an aspect of the present. For example, any variation or combination of features shown and described herein could be employed to form a pair of strips that may be connected by a bridge of material. In addition, while the bridge 120 is illustrated as extending transversely between the strips 100 and 102, the strips also could be connected together end-to-end. Further, the bridge 120 could be formed of connecting means other than the same tissue material that forms the respective strips 100 and 102.

When the interconnected pair of strips has been selected for use with a surgical stapler, the bridge 120 may be cut to separate the strips from each other, such as shown in FIG. 7. The individual strips 100 and 102 may then be applied to opposed jaws of a surgical stapler, such as described herein.

FIGS. 8 and 9 illustrate an example of part of a surgical stapler 150 to which one or more strips of tissue material, in accordance with the present invention, may be applied to facilitate sealing tissue. The surgical stapler 150 includes a pair of opposed and substantially parallel jaws 152 and 154, which are connected by a support 156 attached at proximal ends of the jaws. The jaws 152 and 154 are moveable relative to each other, such as to clamp tissue therebetween, as in known in the art. For example, part of the stapler 150 associated with first jaw 152 may move along a guide track 158 associated with the interconnecting support 156.

The first jaw 152 is configured to store staples (not shown), which may be projected through a face 160 of the jaw. The second jaw 154 includes a face 162 that provides an anvil to receive the staples from the first jaw and initiate bending thereof. In particular, the face 162 includes one or more (e.g., four) rows of parallel receptacles 164 for receiving staples from corresponding the rows located at the face of the first jaw 152. A tab or protrusion 166, for example, extends from part of the stapler 150 associated with the first jaw 152.

FIG. 9 illustrates a strip 170 of biocompatible tissue material attached to the surgical stapler 150 in accordance with an aspect of the present invention. An aperture 172 formed through the strip 170 adjacent a first end 174 receives the tab 166, such that the first end of the strip engages part of the tab to hold the first end relative to the first jaw of the stapler 150. A slot 176 formed through the strip 170 receives a distal end 178 of the first jaw 152 to permit an alignment pin (not shown) to extend into a mating receptacle 180 at a distal end 182 of the other jaw 154. Another end 184 of the strip 170 includes an aperture 186 for releasably securing the end relative to the distal end 182 of the second jaw 154, as shown in FIG. 8.

A retaining ring (See, e.g., FIGS. 2 and 3) 190 secures an intermediate portion of the strip 170, which extends between the slot 176 and the second aperture 186, relative to the support 156. For example, the retaining ring 190 may be slid along the second jaw 154 to a desired position around the support 156 or proximal end of the second jaw. The retaining ring 190 segments the intermediate portion of the strip 170 into a generally V-shaped length in which the retaining ring 190 engages the strip to define a vertex 192. The V-shaped portion includes a first leg 194 of tissue extending from the vertex 192 to the slot 176, which leg is aligned substantially coextensively with the face 160 of the first jaw 152. Another leg 196 of tissue extending between the vertex 192 and the aperture 186 is aligned substantially coextensively with the face 162 of the second jaw 154.

The stapler 150 thus may be activated in a known manner after the tissue strip 170 has been applied to the jaws. The staples, in turn, connect the legs 194 and 196 of tissue together, thereby helping seal tissue positioned therebetween.

FIG. 10 illustrates an example of part of another surgical stapler 200 that may be utilized with one or more tissue strips, in accordance with an aspect of the present invention. The stapler 200 includes a pair of opposed and substantially parallel jaws 202 and 204. The jaw 202 is moveable relative to the jaw 204, which is connected to a handle of the stapler 200 by a bracket support 206.

For example, the first jaw 202 may be moveable in a direction substantially perpendicular to a face 208 of the second jaw 204, such as along substantially parallel alignment rods 210, which may be located at opposite longitudinal ends of the stapler 200. In particular, one alignment rod 210 may be moveable through a bore extending through a distal end 212 of the jaw 202 in a direction generally perpendicular to the faces 208 and 214 of the jaws. The alignment rod 210 is removably insertable into a receptacle 216 at a distal end 218 of the second jaw 204. When the alignment rod 210 connects the jaws 202 and 204 (as shown in FIG. 11), it facilitates proper alignment of the jaws to ensure proper stapling action.

Figure 11:
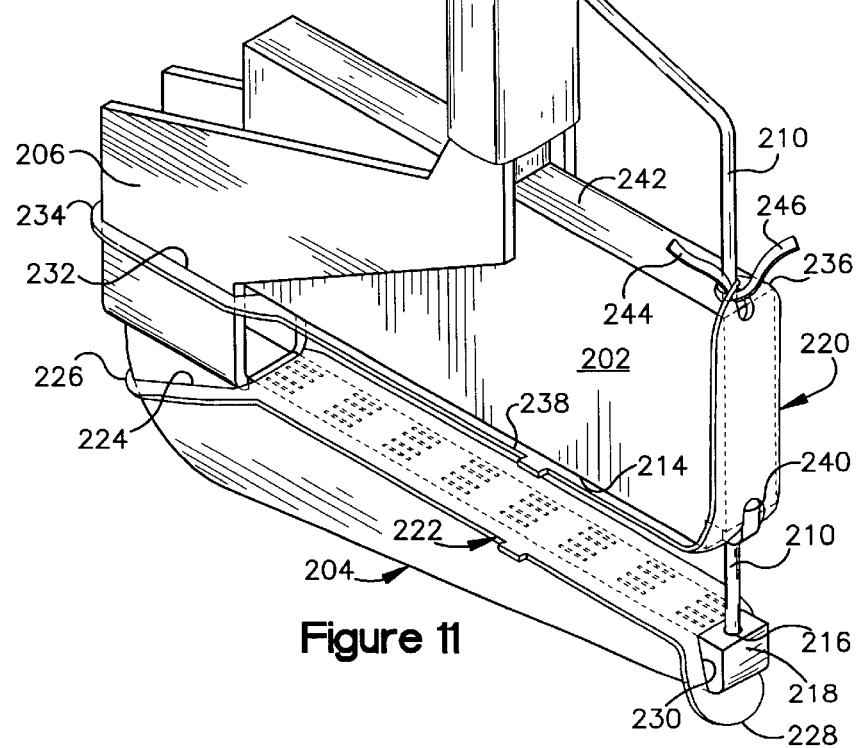
FIG. 11 depicts a biological tissue strip attached to the surgical stapler of FIG. 10 for use in accordance with the present invention.

FIG. 11 illustrates a pair of tissue strips 220 and 222 applied to the stapler 200 of FIG. 10 in accordance with an aspect of the present invention. For example, one tissue strip 220 is applied to the first jaw 202 and the other strip 222 is applied to the second jaw 204, such that the jaws may be urged toward each other to facilitate sealing of tissue interposed between the strips. The individual strips 220 and 222, for example, may be obtained by separating a pair of interconnected strips, such as shown and described with respect to FIGS. 6 and 7.

By way of illustration, the tissue strip 222 includes an aperture 224 at one end 226 that may be urged along the second jaw 204 to a position around a proximal part of the second jaw adjacent the support bracket 206, as shown in FIG. 11. The other end 228 of the strip 222 also includes an aperture 230 that is folded in a direction away from the first jaw 202 to receive the distal end 216 of the second jaw. The receptacle 216 remains free of obstruction and operative to receive the part of the alignment rod 208, such as after both strips 220 and 222 have been attached to the stapler 200 in a desired manner.

The other strip 220 also includes an aperture 232 formed through the strip near one end 234, which receives part of the support bracket 206. For example, the second jaw 204 may be urged through the aperture 234 and the end of the strip slid along the length of the second jaw and over part of the bracket 206. The other end 236 of the strip 220 is urged away from the bracket 206, such that an intermediate portion 238 of the strip, which extends between the aperture 232 and a slot 240, is aligned substantially coextensively with the face 214 of the first jaw 202. The slot 240 is positioned over the distal end 212 of the first jaw 202 to permit the alignment rod 210 to traverse through the slot and into the receptacle 216. The end 236 of the strip is urged away from the second jaw 204 and secured at an opposed side 242 of the first jaw 202. For example, the proximal end 236 of the strip 220 includes ribbons (or cords) 244 and 246 that are tied around the alignment rod 210. By tying the cords 244 and 246 around the rod 210, the end 236 of the strip 220 is held at a desired position relative to the first jaw 202. The alignment rod 210 may be moveable when tied, such that the rod may be urged into the receptacle 216 of the second jaw 204, as shown in FIG. 10.

Figure 12:
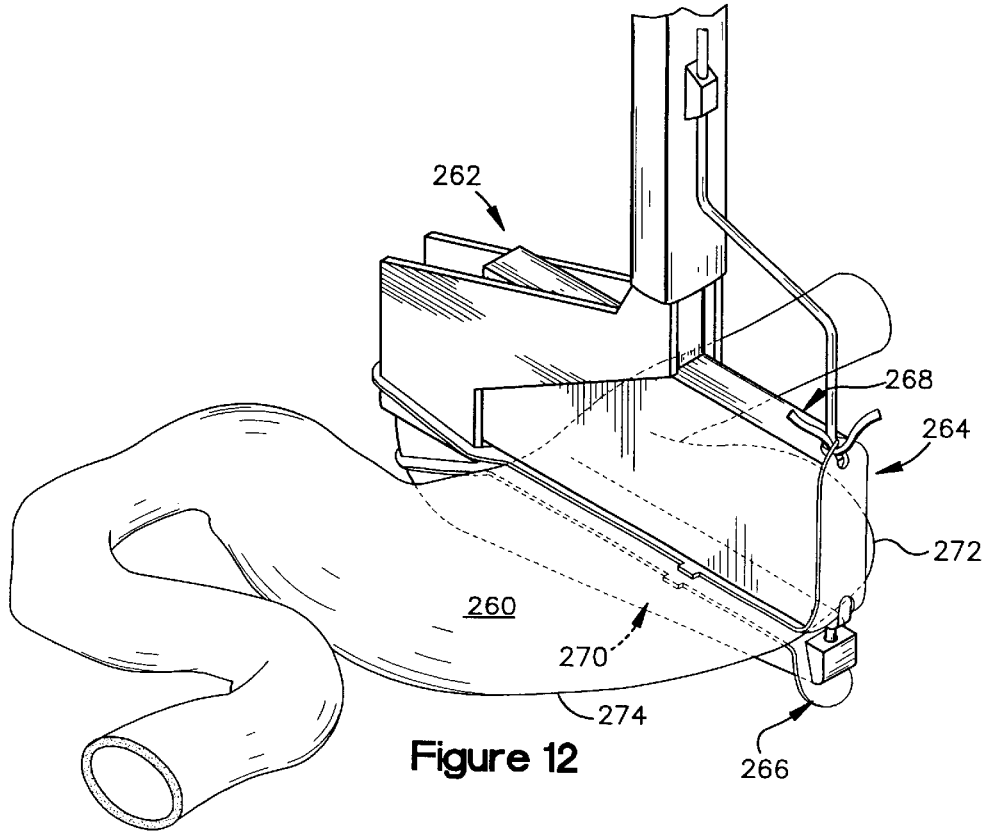
FIG. 12 is an example of biological tissue being applied to part of a stomach with a surgical stapler in accordance with the present invention.
Figure 13:
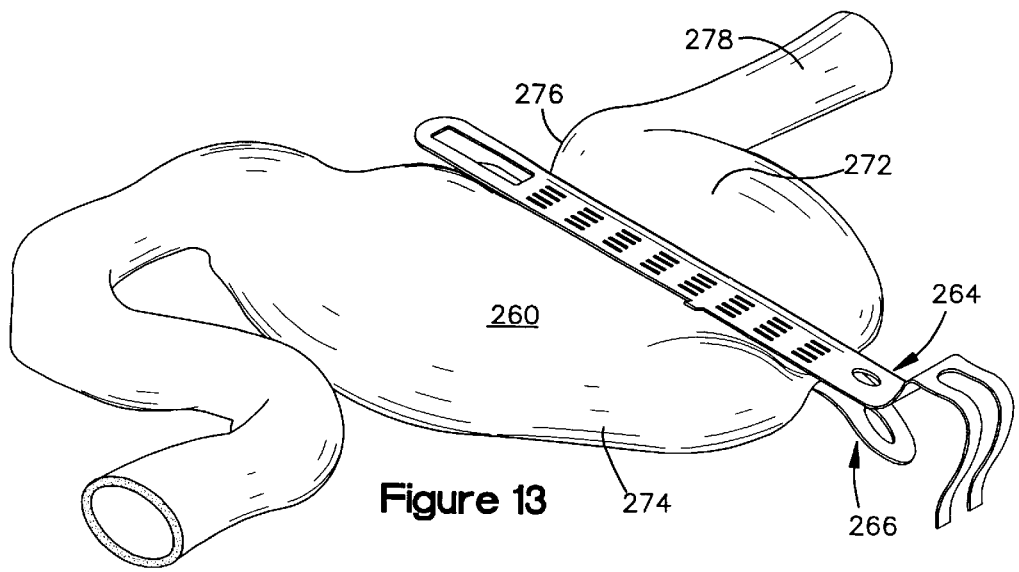
FIG. 13 is an example of the biological tissue applied to the stomach in accordance with the present invention.

FIGS. 12 and 13 depict an example in which a portion of a stomach 260 is stapled with a surgical stapler 262 employing a pair of tissue strips 264 and 266, such as part of a gastric bypass procedure in accordance with an aspect of the present invention. It is to be appreciated that the illustrated dimensions and relative size between the stomach 260 and the stapler 262 is for purposes of illustration, as the relative size will vary as a function of the stomach size of each patient.

Referring to FIG. 12, the combination of stapler 262 and tissue strips 264 and 266 is substantially similar to that shown and described with respect to FIG. 11. For example, the tissue strips 264 and 266, which may have been interconnected by bridge of material, are mounted to opposed jaws 268 and 270 of the stapler 262. A portion of the stomach 260 is positioned between the jaws 268 and 270 and the respective strips 264 and 266 that cover the opposed faces of the jaws. In FIG. 12, the jaws 268 and 270 are illustrated as being in a generally closed condition, such as after being urged toward each other to sandwich the stomach between the jaws. Accordingly, upon activation of the stapler 262, two or more rows of staples are applied through the strips 264 and 266 and the stomach 260 to substantially seal between proximal and distal portions 272 and 274, respectively, of the stomach, such as shown in FIG. 12. The proximal portion 272 of the stomach 260 thus forms a pouch, which is substantially smaller than the distal portion of the stomach.

By way of illustration an opening may be formed in the proximal part of the stomach 260 adjacent the esophagus 278, which location is indicated at 276 in FIG. 12. The opening may be coupled to part of the small or large intestine to bypass the distal part 274 of the stomach 260.

By way of further example, a surgical stapler and one or more associated tissue strip(s), may be employed to seal and divide and seal part of the small intestine in accordance with an aspect of the present invention. That is, a surgical stapler configured to divide and seal further may employ a cutting mechanism (e.g., a knife) that cuts longitudinally between adjacent rows of sutures to divide the tissue on opposed sides of the cutting mechanism. Alternatively, a surgeon can manually separate proximal and distal portions of the stapled tissue, such as by way of an incision through the small intestine on a distal side of the applied tissue strips or pledgets. The distal portion of the intestinal tract may then be coupled to the opening formed at 276 to enable the flow of gastric products from the pouch defined by the proximal part 272 of the stomach 260 into the remaining length of the intestinal tract.

Those skilled in the art will understand appreciate that other configurations of tissue strips may be utilized as pledgets in combination with a surgical stapler in accordance with an aspect of the present invention. In addition, the combination of a stapler and one or more tissue strips further may be employed to divide and/or seal various types of tissue other than the stomach, such as a lung, liver, vascular tissue (e.g., veins or arteries), in accordance with an aspect of the present invention.

What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A strip for use with a surgical stapler, comprising:
   an elongated sheet of flexible, biocompatible material having a leading end, an intermediate portion extending from the leading end and terminating in a trailing end spaced apart from the leading end;
   a first retaining element operatively associated with the leading end of the sheet;
   a second retaining element operatively associated with the trailing end of the sheet, each of the first and second retaining elements being operative to retain the respective end relative to part of the surgical stapler; and
   an aperture extending through the intermediate portion of the sheet between the first and second retaining elements operative to receive an alignment feature of the surgical stapler.

2. The strip of claim 1, wherein the first retaining element further comprises an aperture extending through the sheet adjacent the leading end of the sheet.

3. The strip of claim 1, wherein the second retaining element further comprises an aperture extending through the sheet adjacent the trailing end of the sheet.

4. The strip of claim 1, wherein at least one of the first and second retaining elements further comprises at least two lengths of flexible material that can be tied together to secure an end of the sheet associated with the at least one of the first and second retaining elements relative to the surgical stapler.

5. The strip of claim 4, wherein the at least two lengths of flexible material further comprises at least two lengths of a suture material attached to and extending from the end of the sheet associated with the at least one of the first and second retaining elements.

6. The strip of claim 4, wherein the at least two lengths of flexible material are defined by an elongated channel intersecting the sheet at the end of the sheet associated with the at least one of the first and second retaining elements, the channel extending longitudinally through the strip and terminating at a location spaced from the end of the sheet associated with the at least one of the first and second retaining elements to define the at least two lengths of flexible material on opposed sides of the elongated channel.

7. The strip of claim 1 wherein the sheet is formed of at least one of animal pericardium and collagen.

8. The strip of claim 1, further comprising a retaining ring operative to releasably secure part of the intermediate portion of the sheet located between the slot and one of the leading and trailing ends relative to the surgical stapler.

9. The strip of claim 1, wherein the sheet defines a first length of the flexible material, the strip further comprising:
   a second length of flexible, biocompatible material having a leading end and a trailing end spaced apart from the leading end by an elongated intermediate portion that extends longitudinally between the leading and trailing ends of the second length of flexible material,
   a first retaining element operatively associated with the leading end of the second length of flexible material;
   a second retaining element operatively associated with the trailing end of the second length of flexible material, each of the first and second retaining elements being operative to retain the respective end relative to part of the surgical stapler; and
   a bridge of material interconnecting the first and second lengths of flexible material, whereby the bridge may be cut to provide a pair of strips for use with the surgical stapler.

10. The strip of claim 9, wherein at least one of the first and second retaining elements of the second length of flexible material further comprises an aperture extending through the second length of material at location near the respective leading or trailing end thereof.

11. The strip of claim 10, wherein the bridge, the first length of flexible material, and the second length of flexible material are formed of the same flexible material.

12. The strip of claim 11 wherein the bridge, the first length of flexible material, and the second length of flexible material formed of at least one of animal pericardium and collagen.

13. The strip of claim 11, wherein the sheet further comprises a biological tissue material having glycerin within the sheet of material so as to render the tissue generally pliable when stored in a dry condition.

14. A tissue system for use with a surgical stapler, comprising:
   a first elongated strip of biocompatible tissue material comprising:

a leading end;
a trailing end spaced apart from the leading end by an elongated intermediate portion of the first strip;
a first retaining element operatively associated with the leading end of the first strip;
a second retaining element operatively associated with the trailing end of the first strip;
wherein each of the first and second retaining elements is operative to retain a respective end of the first strip relative to part of the surgical stapler; and
an aperture extending through the intermediate portion of the first strip at a position between the first and second retaining elements operative to receive an alignment feature of the surgical stapler;
a second elongated strip of biocompatible tissue material comprising:
a leading end;
a trailing end spaced apart from the leading end by an elongated intermediate portion that extends longitudinally between the leading and trailing ends of the second strip;
a first retaining element operatively associated with the leading end of the second strip;
a second retaining element operatively associated with the trailing end of the second strip; and
wherein each of the first and second retaining elements of the second strip is operative to retain a respective end of the second strip relative to part of the surgical stapler; and
a bridge of material interconnecting the first and second strips, whereby the bridge may be cut to provide a pair of separate strips for use with the surgical stapler.

15. The tissue system of claim 14, wherein the first strip, the second strip and the bridge are formed of a biological tissue material.

16. The tissue system of claim 15 wherein the biological tissue material further comprises at least one of animal pericardium and collagen.

17. The tissue system of claim 14, wherein at least one of the first and second retaining elements of the first and second strips further comprises an aperture extending through the respective strip at a location near the leading or trailing end thereof.

18. The tissue system of claim 14, wherein at least one of the first and second retaining elements of the first and second strips further comprises at least two elongated cords of material that extend from an associated end of the respective strip, whereby the cords may be tied around part of the surgical stapler.

19. The tissue system of claim 18, wherein the cords are integrally formed of the same material as the respective strip from which the cords extend.

20. The tissue system of claim 14, wherein the each of the first and second strips comprises a biological tissue material having glycerin within the respective strips so as to render the tissue generally pliable when stored in a dry condition.

21. A system to divide and seal tissue, comprising:
an elongated strip of biocompatible flexible material, comprising:
a leading end;
a first retaining element operatively associated with the strip and located near the leading end;
a trailing end spaced from the leading end by an elongated intermediate section of the strip;
a second retaining element operatively associated with the strip and located near the trailing end; and
an aperture extending through the intermediate section of the strip at a location positioned between the first and second retaining elements; and
a surgical stapler, comprising:
first and second jaws mounted relative a handle thereof for movement relative to each other between open and closed positions, the first and second jaws having opposing faces that extend between distal and proximal ends of the respective jaws;
the first and second retaining elements releasably securing the strip relative at least one of the first and second jaws, such that the intermediate section of the strip extends generally coextensive with the face of the at least one of the first and second jaws, an alignment rod near a distal end of the stapler being aligned for movement through the aperture of the strip to facilitate operation of the stapler to drive staples through the intermediate section of the strip.

22. The system of claim 21, wherein at least one of the first and second retaining elements further comprises an aperture extending through the strip at a location near a respective one of the leading and trailing ends.

23. The system of claim 21, further comprising a retaining ring operative to releasably secure part of the intermediate portion of the strip, which is located between the slot and one of the leading and trailing ends, relative to the surgical stapler.

24. The system of claim 21, wherein the strip defines a first strip, the system further comprising:
a second elongated strip of biocompatible tissue material comprising:
a leading end;
a trailing end spaced apart from the leading end by an elongated intermediate portion that extends longitudinally between the leading and trailing ends of the second strip;
a first retaining element operatively associated with the leading end of the second strip;
a second retaining element operatively associated with the trailing end of the second strip;
wherein the first and second retaining elements of the second strip are operative to retain respective ends of the second strip relative to the second jaw of the surgical stapler, the first and second retaining elements of the first strip being operative to retain respective ends of the second strip relative to the first jaw of the surgical stapler so that an alignment rod near the distal end of the stapler is aligned for movement through the aperture of the strip; and
a bridge of material interconnecting the first and second strips, whereby the bridge may be cut to provide a pair of strips for positioning on different jaws the surgical stapler.

25. A method of using the system of claim 24, comprising:
cutting the bridge to separate the first and second strips from each other;
attaching the first retaining element of the first strip relative to the proximal end of the first jaw;
attaching the second retaining element of the first strip relative to the distal end of the first jaw, such that a substantial portion of the intermediate section of the first strip is coextensive with the face of the first jaw;
attaching the first retaining element of the second strip relative to the proximal end of the second jaw; and
attaching the second retaining element of the second strip relative to the distal end of the second jaw, such that a substantial portion of the intermediate section of the second strip is coextensive with the face of the second jaw.

26. The method of claim 25, further comprising:

inserting at least part of the first and second jaws and the first and second strips into a body of a warm blooded animal, such that a selected part of the tissue is interposed between the first and second jaws;

actuating the stapler to urge the jaws toward each other and drive staples through the first and second strips and the selected part of the tissue located between the first and second strips; and distorting the staples to secure the selected part of the tissue between the first and second strips.

27. A method of using the system of claim 21, comprising:

attaching the first retaining element of the strip to part of the surgical stapler associated with the first jaw to hold the leading end of the strip near the distal end of the first jaw, such that the slot is positioned to permit movement of the alignment rod through the slot;

attaching the second retaining element of the strip to part of the surgical stapler associated with the second jaw to hold the trailing end of the strip near the distal end of the second jaw;

positioning a retaining ring over the strip and one jaw of the first and second jaws to releasably secure part of the intermediate section of the strip relative to part of the stapler near the proximal end of the one jaw, such that a first portion of the strip extending between the retaining ring and the leading end of the strip extends generally coextensively with the face of the first jaw and a second portion of the strip extending between the retaining ring and the trailing end of the strip extends generally coextensively with the face of the second jaw.

28. The method of claim 27, further comprising:

inserting at least part of the jaws and the associated strip attached thereto into a body of a warm blooded animal, such that a selected part of the tissue is interposed between the first and second portions of the strip;

actuating the stapler to urge the jaws toward each other and drive staples through the first and second portions of the strip and the selected part of the tissue located between the first and second portions of the strip; and distorting the staples to secure the selected part of the tissue between the first and second portions of the strip.

* * * * *